(12) United States Patent
Phillion et al.

(10) Patent No.: US 6,632,950 B2
(45) Date of Patent: Oct. 14, 2003

(54) PROCESS FOR THE PREPARATION OF DERIVATIVES OF 4-AMINO-3-HYDROXYPYRROLE-2-CARBOXYLIC ACID

(75) Inventors: Dennis P. Phillion, St. Louis, MO (US); Megh Singh, Bridgeton, MO (US)

(73) Assignee: Pharmacia Corporation, Chicago, IL (US)

( * ) Notice: Subject to any disclaimer, the term of this patent is extended or adjusted under 35 U.S.C. 154(b) by 0 days.

(21) Appl. No.: 09/899,715

(22) Filed: Jul. 5, 2001

(65) Prior Publication Data

US 2002/0042522 A1 Apr. 11, 2002

Related U.S. Application Data

(60) Provisional application No. 60/216,101, filed on Jul. 6, 2000.

(51) Int. Cl.[7] .............................................. C07D 207/02
(52) U.S. Cl. ...................................................... 548/535
(58) Field of Search ......................................... 548/535

(56) References Cited

FOREIGN PATENT DOCUMENTS

| WO | WO 97/30975 | 8/1997 |
| WO | WO 98/37066 | 8/1998 |

OTHER PUBLICATIONS

Narkunan, K. et al., "Practical Synthesis of Active Esters of 4–Alkoxycarbonylamino–3–methoxy–pyrrole–2–carboxylic acid," Synthesis 2000, Jan. 5, 2000, No. 5, pp. 673–676.
Baird, E., et al., "Solid Phase Synthesis of Polyamides Containing Imidazole and Pyrrole Amino Acids," J. Am. Chem. Soc., Mar. 5, 1996, 118, pp. 6141–6146.
Urbach, A., et al., "Sequence Selectivity of 3–Hydroxypyrrole/Pyrrole Ring Pairings in the DNA Minor Groove," J. Am. Chem. Soc., Aug. 23, 1999, 121, pp. 11621–11629.
Urbach, A., "Sequence Selectivity of 3–Hydroxypyrrole/Pyrrole Ring Pairings in the DNA Minor Groove," J. Am. Chem. Soc., 1999, pp. 11621–11629, vol. 121, No. 50, Published on Web Dec. 1, 1999.
Prolinx, Inc., "Sequence Seekers™," Mar. 28, 1999, 4 pages.
Momose, et al., "3–Hydroxypyrrole. I. A General Synthetic Route to 4,5–Unsubstituted Alkyl 3–Hydroxypyrrole–2–Carboxylates," Chem. Pharm. Bull., 1979, 26(7), 2224–2238.

*Primary Examiner*—Joseph K. McKane
*Assistant Examiner*—Andrea D. Small
(74) *Attorney, Agent, or Firm*—Senniger, Powers, Leavitt & Roedel

(57) ABSTRACT

Novel processes and intermediates are provided for the synthesis of derivatives of 4-amino-3-hydroxypyrrole-2-carboxylic acids that are useful as monomers for polyamides capable of binding dsDNA. According to one preferred reaction scheme, an alkyl alkoxymethylene nitroacetate (Formula VIII) is prepared by reaction of a trialkyl orthoformate or orthoacetate with a nitroacetate ester in the presence of a carboxylic anhydride. The compound of Formula VIII is condensed with an N-substituted glycine to yield an N-substituted (2-nitro-2-alkoxycarbonyl)vinyl glycinate ester (Formula VII). Ring closure in the presence of an alkali metal alkoxide yields a 4-nitro-3-hydroxypyrrole-2-carboxylic ester (Formula V). After blocking of the 3-hydroxy group to produce a further intermediate (Formula IV), the 4-nitro group is reduced to a 4-amino group (Formula III), and the 4-amino group is then blocked by reaction with a dicarbonate diester to produce the fully blocked intermediate (Formula II). Saponification of the 2-carboxylic acid ester yields a monomer having a free 2-carboxylic ester moiety (Formula I).

8 Claims, No Drawings

PROCESS FOR THE PREPARATION OF DERIVATIVES OF 4-AMINO-3-HYDROXYPYRROLE-2-CARBOXYLIC ACID

This application claims benefit of Ser. No. 60/216,101 Jul. 6, 2000.

BACKGROUND OF THE INVENTION

This invention relates the preparation of compounds useful as monomers in the preparation of polyamides, and more particularly to novel methods and novel intermediates for the preparation of 3-hydroxypyrrole monomers for polyamides that are useful in nucleotide sequence recognition.

Certain polyamides derived from heteroaryl amino acid monomers are capable of binding to dsDNA and have been found useful in the recognition of nucleotide sequences as well as other applications. See, for example, Dervan U.S. Pat. No. 5,998,140 and Urbach et al., "Sequence Selectivity of 3-Hyroxypyrrole/Pyrrole Ring Pairings in the DNA Minor Groove," *J. Am. Chem. Soc.,* 1999, 121, 11621–11629. Polyamides containing various combinations of amino acid units respectively comprising pyrrole, hydroxypyrrole and imidazole moieties have been found particularly suitable for this purpose. G/C base pairs have been found to be complemented by the juxtaposed combination of N-methylimidazole/N-methylpyrrole, C/G pairs by N-methylpyrrole/N-methylimdazole, and T/A pairs by N-methylpyrrole/N-methylpyrrole or N-methyl-3-hydroxypyrrole/N-methylpyrrole. Polyamides containing these combinations can form intracellular complexes by complementation with sequences in dsDNA, the complementation being advantageously facilitated by providing a hairpin turn in the polyamide, or may be accomplished by using two amide oligomers.

Methods for the preparation of hairpin polyamide polymers and monomers useful in their synthesis are described in the above-cited Dervan patent and Urbach et al. article. An earlier article of Momose et al., "3-Hydroxypyrrole. I. A General Synthetic Route to 4,5-Unsubstituted Alkyl 3-Hydroxypyrrole-2-carboxylates," *Chem. Pharm. Bull.,* 26(7), 2224–2238 (1979) also describes methods for the preparation of amino acids derivatives of 3-hydroxypyrrole.

A particularly preferred monomer for the preparation of heteroaryl polyamides is the 3-hydroxypyrrole derivative corresponding to the formula

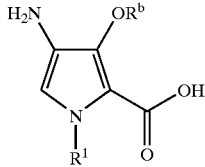

(Formula XXV)

wherein $R^1$ is typically methyl, and $R^b$ a protective group to block side reactions during the course of the polyamide synthesis. Urbach describes a method for producing such monomer in which ethyl 4-carboxyl-3-hydroxy-1-methylpyrrole-2-carboxylate is reacted with diphenylphosphoryl azide in the presence of triethylamine in acetonitrile to form the isocyanate which is thereafter reacted with benzyl alcohol to produce ethyl 4-[(benzyloxycarbonyl)amino]-3-hydroxy-1-methyl-2-carboxylate. The latter compound is reacted with methyl iodide in the presence of 4-dimethylaminopyridine and potassium carbonate in acetone to produce the 3-methoxy derivative, after which di(t-butyl) carbonate and 10% Pd/C are added to the mixture, and the mixture stirred under a hydrogen atmosphere to produce ethyl 4-[(t-butoxycarbonyl)amino]-3-methoxy-2-carboxylate. The latter compound is saponified to the 2-carboxylic acid, which is useful as a monomer in the synthesis of polyamides of the type effective in the sequence identification procedures described in Dervan U.S. Pat. No. 5,998,140 and the Urbach article.

In the synthesis of Urbach, the steps required to introduce a blocked 4-amino group have an adverse tendency to decarboxylate at the 4-position, especially in the presence of water. Thus, for satisfactory monomer synthesis per the Urbach route, it is necessary that measures be taken to substantially exclude moisture from the reaction mixture. Moreover, the synthesis described by Urbach involves release of nitrogen gas from the reaction mixture. Unless the reaction conditions are carefully controlled, the rate of gas release may potentially pose an operational hazard, particularly in large scale synthesis.

In synthesis of the polyamides, it is also important that the 3-hydroxy group be protected so that it does not participate in side reactions which produce branched or cross-linked polyamides that are less suitable for nucleotide recognition than are the unbranched polyamides described by Dervan and Urbach. After polymerization, the O-methyl group is removed since the free hyroxyl is the desired structure for use in nucleic acid binding. Although O-methylation provides very satisfactory protection of the 3-hydroxy group during the polymerization reaction, and is a preferred protective procedure for many applications, the O-methyl group can be difficult to remove after the polymerization is complete. It would, therefore, be useful to provide other protective groups which are effective to prevent branching or cross-linking during the polymerization but more susceptible to removal from the polyamide product.

SUMMARY OF THE INVENTION

Among the objects of the present invention may be noted the provision of a method for the preparation of heteroaryl amino acid monomers useful in the preparation of polyamides; the provision of such a method which avoids the loss of desired substituents from the heteraryl ring during the course of synthesis reactions; the provision of such a process which can be constantly operated without rapid gas release from any reaction step; the provision of alternative protective groups at the 3-position of a 3-hydroxypyrrole derivative; and the provision of novel intermediates useful in the synthesis of monomers for bioactive polyamides.

Briefly, therefore, the invention is directed to a process for the preparation of a compound of Formula II Formula II

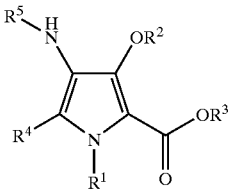

wherein $R^1$ and $R^3$ substituted or unsubstituted alkyl (preferably $C_1$ to $C_6$), alkenyl (preferably $C_2$ to $C_6$), alkynyl (preferably $C_2$ to $C_6$), aralkyl, or aryl; $R^2$ is substituted or unsubstituted alkyl, alkenyl, alkynyl, aralkyl, aryl, alkylcarbonyl, haloalkylcarbonyl, aralkylcarbonyl, arylcarbonyl, alkoxycarbonyl, alkenoxycarbonyl, alkynoxycarbonyl, arylkoxycarbonyl, aryloxycarbonyl or substituted silyl; $R^4$ is hydrogen or methyl; and $R^5$ is a carbamate-forming blocking group. The process comprises reducing the nitro group of a compound of Formula IV

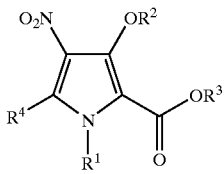
(Formula IV)

wherein $R^1$, $R^2$, $R^3$ and $R^4$ are as defined above, thereby producing a compound of Formula III

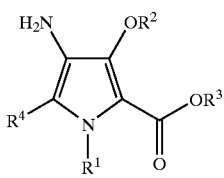
(Formula III)

wherein $R^1$, $R^2$, $R^3$ and $R^4$ are as defined above. The compound of Formula III is contacted with a blocking group reagent thereby substituting a blocking group on the 4-amino group.

The invention is further directed to a process for the preparation of the compound of Formula III. The process comprises reducing the nitro compound of a group of Formula IV.

The invention is further directed to a process for the preparation of the compound of Formula IV. In this process a 3-hydroxypyrrole derivative corresponding to Formula V

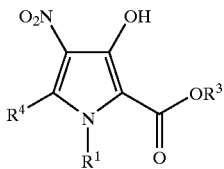
(Formula V)

or the keto tautomer of the 3-hydroxypyrrole derivative, the keto tautomer corresponding to the structure

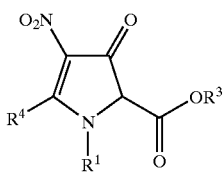
(Formula Va)

wherein $R^1$, $R^3$ and $R^4$ are as set forth above, with a blocking reagent effective to form an —$OR^2$ group at the 3-position of the compound of Formula V.

The invention is further directed to a process for the preparation of a 3-hydroxypyrrole derivative corresponding to Formula V or the keto tautomer thereof (as corresponding to Formula Va). The process comprises contacting a compound of Formula VII with a reagent effective for promoting ring closure. The compound of Formula VII corresponds to the structure

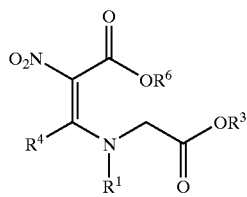
(Formula VII)

wherein $R^1$, $R^3$ and $R^4$ are as defined above and —$OR^6$ is a leaving group.

The invention is further directed to a process for the preparation of a compound corresponding to Formula VII. In this process a compound of Formula VIII is reacted with an N-substituted glycine ester corresponding to Formula IX. The compound of Formula VIII has the structure

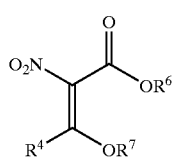
(Formula VIII)

wherein $R^1$ and $R^6$ are as defined above and $R^7$ is a leaving group. The compound of Formula IX has the structure

$R^1NHCH_2C(O)OR^3$ wherein $R^1$ is as defined above.

The invention is further directed to a process for the preparation of the compound corresponding to Formula XI

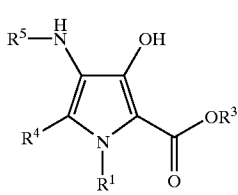
(Formula XI)

or the keto tautomer thereof

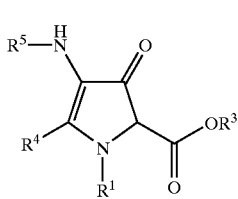
(Formula XIa)

wherein $R^1$, $R^3$, $R^4$ and $R^5$ are as defined above. The process comprises contacting a compound of Formula XII and/or the keto tautomer thereof with a blocking group reagent thereby substituting a blocking group on the 4-amino group. The compound of Formula XII has the structure

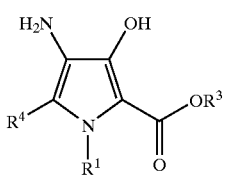
(Formula XII)

The keto tautomer of Formula XII corresponds to Formula XIIa

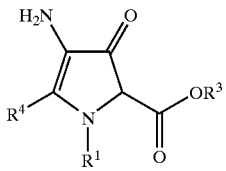
(Formula XIIa)

In both Formula XII and Formula XIIa, $R^1$, $R^3$ and $R^4$ are as defined above.

The invention is further directed to a process for the preparation of a compound of Formula XII. The process comprises reducing a nitro group of a compound of Formula V or the keto tautomer of Formula V.

The invention is further directed to a compound corresponding to Formula XIV

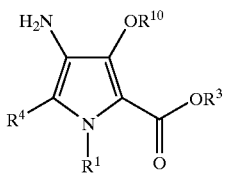
(Formula XIV)

wherein $R^{10}$ is selected from among hydrogen, substituted and unsubstituted alkyl (preferably $C_1$ to $C_6$), alkenyl (preferably $C_2$ to $C_6$), alkynyl (preferably $C_2$ to $C_6$), aralkyl, aryl, alkylcarbonyl, haloalkylcarbonyl, aralkylcarbonyl, arylcarbonyl, alkoxycarbonyl, alkenoxycarbonyl, alkynoxycarbonyl, aralkoxycarbonyl, aryloxycarbonyl and substituted silyl; and $R^1$, $R^3$ and $R^4$ are as defined above.

The invention is further directed to a compound corresponding to Formula XV

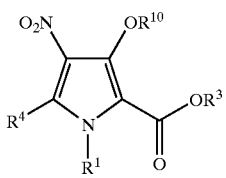
(Formula XV)

wherein $R^1$, $R^3$, $R^4$ and $R^{10}$ are as defined above; and the keto tautomer of Formula XV wherein $R^{10}$ of Formula XV would otherwise be hydrogen.

The invention is further directed to a compound corresponding to Formula VII

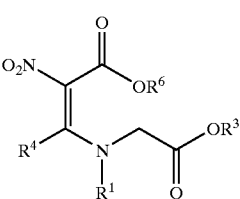
(Formula VII)

wherein $R^1$, $R^3$, $R^4$ and $R^6$ are as defined above.

The invention is further directed to a process for the preparation of a compound corresponding to Formula XVI

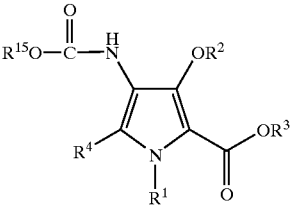
(Formula XVI)

wherein $R^{15}$ is selected from among alkyl (preferably $C_1$ to $C_6$), alkenyl (preferably $C_2$ to $C_6$), alkynyl (preferably $C_2$ to $C_6$), aralkyl and aryl; and $R^1$, $R^2$, $R^3$ and $R^4$ are as defined above. The process comprises contacting a compound of Formula III with a carbonyl compound under conditions effective for the reaction of the 4-amino group of the compound of Formula III with the carbonyl compound, to produce the compound of Formula XVII

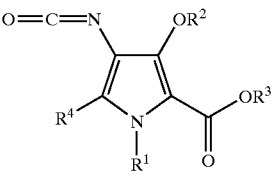
(Formula XVII)

and contacting the compound of Formula XVII with an alcohol of Formula XVIII $R^{15}OH$ wherein $R^{15}$ is selected from unsubstituted alkyl (preferably $C_1$ to $C_6$), alkenyl (preferably $C_2$ to $C_6$), alkynyl (preferably $C_2$ to $C_6$), aralkyl, and aryl; and $R^1$, $R^2$, $R^3$ and $R^4$ are as defined above.

The invention is further directed to a process for the preparation of a compound of Formula XIX

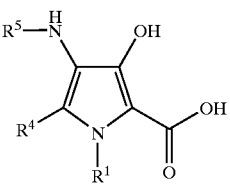
(Formula XIX)

wherein $R^1$, $R^4$ and $R^5$ are as defined above; or the keto tautomer of such compound of Formula XIX. The process comprises hydrolyzing a compound of Formula XX by contacting it with a base. The compound of Formula XX has the structure

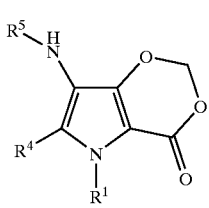

(Formula XX)

wherein $R^1$, $R^4$ and $R^5$ are as defined above.

The invention is further directed to the preparation of a compound of Formula XX. The process comprises reacting a compound of Formula XXI with a blocking reagent

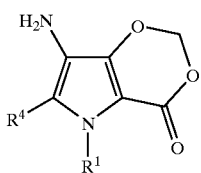

(Formula XXI)

wherein $R^1$ and $R^4$ are as defined above.

The invention is further directed to the preparation of a compound of Formula XXI. The process comprises reducing the nitro group of a compound of Formula XXII

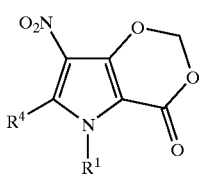

(Formula XXII)

wherein $R^1$ and $R^4$ are as defined above.

The invention is further directed to a process for the preparation of a compound corresponding to Formula XXII

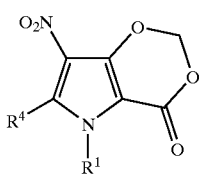

(Formula XXII)

wherein $R^1$ and $R^4$ are as defined above. The process comprises reacting a compound of Formula V or the keto tautomer thereof with paraformaldehyde in the presence of a nitrogenous base.

The invention is further directed to a compound corresponding to the Formula XXII wherein $R^1$ and $R^4$ are as defined above.

The invention is further directed to a compound corresponding to Formula XXI

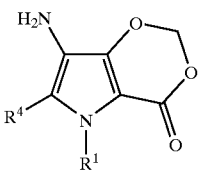

(Formula XXI)

wherein $R^1$ and $R^4$ are as defined above.

The invention is further directed to a compound corresponding to Formula XX

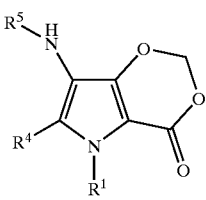

(Formula XX)

wherein $R^1$, $R^4$ and $R^5$ are as defined above.

The invention is further directed to a compound corresponding to Formula XXIII (Formula XXIII)

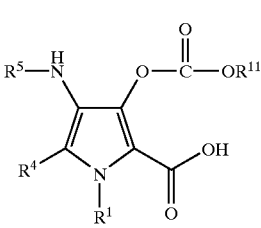

wherein $R^1$, $R^4$ and $R^5$ are as defined above; and $R''$ is selected from the group consisting of alkyl (preferably $C_1$ to $C_6$), alkenyl (preferably $C_2$ to $C_6$), alkynyl (preferably $C_2$ to $C_6$), aralkyl and aryl. $R^5$ is preferably

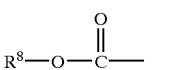

where $R^8$ is selected from among substituted and unsubstituted alkyl (preferably $C_1$ to $C_6$), alkenyl (preferably $C_2$ to $C_6$), alkynyl (preferably $C_2$ to $C_6$), aralkyl and aryl.

The invention is further directed to a compound corresponding to the formula (Formula XXVI)

where $R^1$, $R^4$, $R^5$ and $R^{11}$ are as defined above.

The invention is further directed to a compound corresponding to Formula XXIV

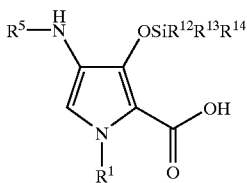

(Formula XXIV)

wherein $R^1$, $R^4$ and $R^5$ are as defined above; and $R^{12}$, $R^{13}$ and $R^{14}$ are independently alkyl (preferably $C_1$ to $C_6$).

Other objects and features will be in part apparent and in part pointed out hereinafter.

DESCRIPTION OF THE PREFERRED EMBODIMENTS

In accordance with the present invention, novel and advantageous processes are provided for the synthesis of heteroaryl amino acids. Novel intermediates are produced in the course of the various syntheses of the invention. The heteroaryl amino acid products of these syntheses are useful in the preparation of polyamides, e.g., hairpin polyamides, which bind to the minor groove of DNA and are effective for the identification of polynucleotide sequences.

As noted, the monomers ultimately used in the synthesis of dsDNA-complementing polyamides are 4-amino-3-hydroxy-2-carboxylic acids derivatives corresponding to the Formula XXV

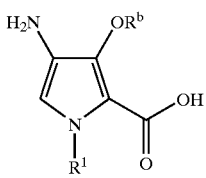

Formula XXV in which the 3-hydroxyl is protected by the $R^b$ blocking group to prevent side reactions during polyamide synthesis. Although the monomers are typically unsubstituted in the 5-position, a substituent may optionally be present at this position provided that it creates no problems in polymerization arising from steric hindrance, electronic configuration, or reactivity. Preferably, the monomers are synthesized to also comprise a blocking substituent on the 4-amino group, i.e., the monomers correspond to the structure of Formula I

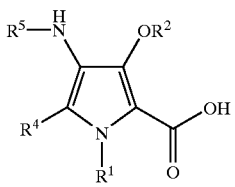

(Formula I)

wherein $R^1$, $R^2$, $R^4$ and $R^5$ are as defined above. In the course of solid phase polyamide synthesis, the $R^5$ blocking group is removed at the N-terminus of the oligoamide immediately prior to coupling the next monomer unit, e.g., by treatment with trifluoroacetic acid.

In accordance with the invention, several alternative process schemes have been discovered for synthesis of 4-nitro-3-hydroxy-2-carboxylate esters and conversion thereof to 4-amino-3-hydroxy-2-carboxyate esters which are protected with blocking substituents at both the 3-position oxygen and and the 4-position nitrogen.

Each of the reaction schemes of the invention produces a monomer having the structure of Formula I

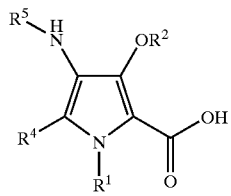

(Formula I)

In the structure of Formula I, $R^1$ may independently be substituted and unsubstituted alkyl, alkenyl or alkynyl, preferably $C_1$ to $C_6$ alkyl, $C_2$ to $C_6$ alkenyl, or $C_2$ to $C_6$ alkynyl, and may also be aralkyl or aryl. For example, $R^1$ may be methyl, ethyl, n-propyl, 1-propyl, n-butyl, 1-butyl, t-butyl, amyl and hexyl, vinyl, allyl, 2-butenyl, 3-pentenyl, ethynyl, phenyl, naphthyl and benzyl. Generally, alkyl groups are preferred, among which ethyl, 1-propyl and t-butyl are more preferred. Most preferably, $R^1$ is methyl.

$R^2$ in Formula I may be selected from among any of the substituents which may constitute $R^1$, and may alternatively be substituted or unsubstituted alkylcarbonyl, aralkylcarbonyl, arylcarbonyl, haloalkylcarbonyl, alkoxycarbonyl, alkenoxycarbonyl, alkynoxcarbonyl, aralkoxycarbonyl, aryloxycarbonyl or substituted silyl. Preferably, $R^2$ is methyl, allyl, or benzyl. Where $R^2$ is further substituted, it may comprise any of the further substituents that are described above for substitution on $R^1$.

$R^4$ in Formula I is ordinarily hydrogen, but may alternatively be methyl.

$R^5$ represents a carbamate-forming blocking group. Preferred blocking groups include t-butoxycarbonyl, fluorenylmethoxycarbonyl, allyloxycarbonyl, trialkylsilyloxycarbonyl, and benzyloxycarbonyl.

The several reaction schemes of the invention are described below.

Reaction Scheme 1

The first reaction scheme is advantageously initiated by the preparation of a precursor compound of Formula VIII

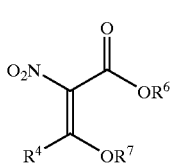

(Formula VIII)

wherein $R^4$ is as defined above, $R^7$ is a suitable leaving group, and —O—$R^6$ is a leaving group subject to removal in a subsequent ring closure reaction. $R^6$ and $R^7$ can be any of the constituents which may constitute $R^3$ as described above. Preferably, $R^6$ and $R^7$ are independently $C_1$ to $C_6$ alkyl, more preferably methyl or ethyl, most preferably ethyl. In the preparation of the compound of Formula VIII, a nitroacetate ester compound corresponding to Formula X may be reacted with a trialkyl orthoformate or trialkyl orthoacetate, (e.g., triethyl orthoformate) and a carboxylic anhydride, preferably acetic anhydride. The substrate of Formula X has the structure $$O_2NCH_2C(O)OR^6 \quad \text{(Formula X)}$$

where $R^6$ is as defined above. Preferably, $R^6$ is methyl or ethyl, more preferably ethyl. Generally, the preferred orthocarboxylate ester reactant comprises a lower alkyl ester, e.g., a trimethyl or triethyl ester. In the synthesis of heteroaryl amino acid monomers, an orthoformate triester is typically preferred. The reaction between the nitroacetate ester, orthoformate triester and acetic anhydride yields a compound of Formula VIII in which $R^4$ is hydrogen. Use of the orthoacetate triester yields the corresponding compound in which $R^4$ is methyl. The reaction is conducted under temperature and pressure conditions effective to drive off the by-product alcohol. Where a triethyl ester is used, the reaction may conveniently be conducted at atmospheric pressure and a temperature of between about 100° and about 175° C. Preferably, both orthoformate ester and acetic anhydride are introduced into the reaction zone in molar excess with respect to the nitroacetate ester substrate. After the reaction is complete, excess orthocarboxylate ester and carboxylic anhydride are removed, preferably under reduced pressure to yield the intermediate of Formula VIII.

In the next step of reaction scheme 1, the intermediate of Formula VIII is condensed with an N-substituted glycine reagent of Formula IX $$R^1NHCH_2C(O)OR^3 \quad \text{(Formula IX)}$$

wherein $R^3$ is as defined above, to yield a further intermediate of Formula VII

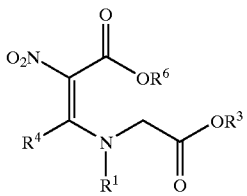

(Formula VII)

wherein $R^1$, $R^3$, $R^4$ and $R^6$ are as defined above. Preferably, the N-substituted glycine reagent of Formula IX is a sarcosinate ester (i.e., $R^1$ is methyl), more preferably ethyl sarcosinate ($R^3$ is ethyl). Preferred moieties which can constitute $R^3$ include those described above as groups which can constitute $R^1$. The reaction is preferably conducted with substantially equimolar proportions of the compound of Formula VIII and the N-substituted glycine ester of Formula IX. The temperature of the reaction is not critical. Conveniently, it is conducted at room temperature under agitation and cooling for removal of the exothermic heat of reaction. Preferably, the reactants are co-fed to the reaction zone gradually over time, or one reactant is charged initially to the reaction zone and the other gradually added over time, so that the reaction rate and exotherm proceed at a controlled rate. If desired, the reaction can be conducted in a solvent medium such as water, dimethylsulfoxide, dimethylformamide, a lower alcohol such as ethanol or isopropanol, an aromatic solvent such as benzene, toluene, or xylene, or an ester such as ethyl acetate. However, maximum reactor payloads are provided where the reactants are introduced neat. Reaction time is typically under 2 hours. After the reaction is complete, by-product alcohol ($R^7OH$) is removed by evaporation, yielding an oily liquid product.

Where the reaction of the compound of Formula VIII with the compound of Formula IX is conducted in a solvent, a product of enhanced purity may be obtained by extracting the product from the reaction medium, and then driving off the extraction solvent. For example, where the reaction is conducted in water, the product of Formula VII may be extracted in a more volatile solvent, e.g., ethyl acetate or an aromatic solvent. Where DMSO is the reaction medium, the product may be extracted with water. In the latter instance, the product may be recovered either by diluting water and back extracting into a more volatile solvent and recovering the product by driving off the latter solvent. The DMSO remains in the aqueous phase.

The compound of Formula VII is a novel compound useful in the synthesis of polyamides, and potentially useful as a multi-purpose intermediate and even as a monomer useful in preparation of polymers by addition polymerization. Where the compound of Formula VII is used in the synthesis of polyamides for binding to DNA, the substituents thereof are preferably selected on the basis outlined above. Most preferably $R^1$ is methyl and $R^3$ is ethyl. For such applications, the substituent $R^6$, which is removed in a subsequent reaction step, is preferably $C_1$ to $C_6$ alkyl, most preferably methyl, propyl, isopropyl, n-butyl, or t-butyl, most preferably ethyl.

Ring closure of the intermediate of Formula VII yields the further novel intermediate of Formula V

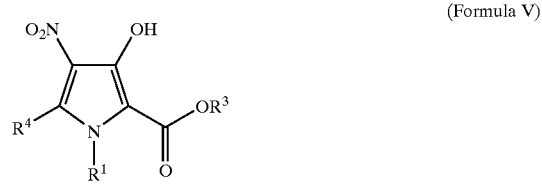

(Formula V)

wherein $R^1$, $R^3$, and $R^4$ are as set forth above. The compound of Formula V can exist in equilibrium with its keto tautomer

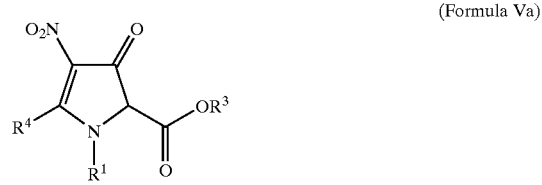

(Formula Va)

For utility as an intermediate in preparation of monomers for polyamides that bind to DNA, there is no practical difference between the tautomers. In preparation of the compound of Formula V and/or Va, the compound of Formula VII is preferably contacted with a base effective for promoting the ring closure reaction. For example, the compound of Formula V/Va may be contacted with an alkali metal alkoxide in the presence of the alcohol, typically the alcohol corresponding to the alkoxide. The reaction may be conducted at ambient or elevated temperature, conveniently at atmospheric reflux in the alcohol medium. Heating may be required to sustain the desired reaction temperature. The alcohol medium is removed under reduced pressure to provide a residue comprising the crude alkali metal salt of the product of Formula V. The residue is taken up in water and acidified, e.g., with dilute sulfuric acid, to precipitate the 3-hydroxypyrrole derivative of Formula V and/or its keto tautomer of Formula Va.

Only the E isomer form of the compound of Formula VII undergoes ring closure to yield the salt of the compound of Formula V. Thus, unreacted Z isomer and reaction by-products are preferably removed from the precipitated compound of Formula V/Va. The precipitate is first separated from the acidified mother liquor by filtration or centrifugation, and washed with water, after which the washed solids are taken up in a solvent, preferably a halogenated solvent such as dichloromethane chloroform or 1,2-dichloroethane. The product may be passed through an adsorbent such as silica gel for further purification. The Formula V/Va product may be further purified, if desired, by recrystallization, e.g., from an ester/alkane solvent mixture.

In an alternative product recovery scheme, the 3-hydroxy compound of Formula V/Va can be precipitated directly by acidification of the reaction solution, after which the precipitate can be taken up in alkaline solution and the product extracted with an organic solvent such as an ether, ester, or halogenated solvent to remove neutral by-products. After acidification of the aqueous phase, the compound of formula IV/IVa can be extracted into an ether, ester or halogenated solvent. Removal of the solvent yields the product of Formula V/Va.

Optionally, bases other than an alkoxide can be used in the cyclization reaction. Certain of the other bases can be used if desired in a process in which a carbanion of Formula VIIa is first produced at low temperatures.

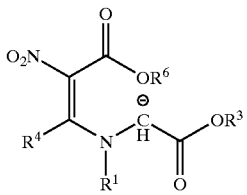

(Formula VIIa)

wherein $R^1$, $R^3$, $R^4$ and $R^5$ are as defined above. For example, the carbanion may be initially produced by reaction in the cold in a solution comprising an organic solvent, the compound of Formula VII, and a base such as, e.g., Li or Na diisopropylamide or Li bis (trimethylsilylamide). Typically, a stable carbanion can be formed at temperatures in the range of −60° C. to −90° C. Warming the solution results in ring closure. This reaction may be conducted in any of a variety of solvents including tetrahydrofuran, benzene, toluene, and DMSO. The resulting solution containing a Li salt of the compound of Formula V may be treated with acid to precipitate the compound of Formula V and/or the tautomer of Formula Va. Formula V/Va product may be refined by taking up the precipitate in aqueous base, and extracting neutral by-products and Z isomer of Formula VII using an organic solvent such as ether, ethyl acetate or other low molecular weight ester, 1,2-dichloroethane or other halogenated solvent.

The compound of Formula V and its tautomer of Formula Va are novel compounds having utility in the synthesis of monomers for polyamides, and potentially for synthesis of other useful products. For use in synthesis of monomers for polyamides that bind to DNA, preferences for the substituents $R^1$ and $R^3$ of the compounds of Formula V/Va are the same as for corresponding substituents of the compounds of Formula VII.

In Reaction Scheme 1, the compound of Formula V and/or the tautomer of Formula Va are reacted with a reagent effective for introducing a blocking group $R^2$ on the 3-hydroxyl, thereby producing a compound of Formula IV

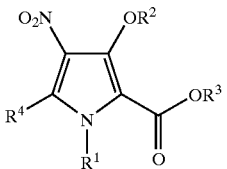

(Formula IV)

where $R^1$, $R^2$, and $R^3$ are defined above. The reagent effective for introducing the blocking group is preferably an etherifying agent corresponding to the formula $(R^2O)_2SO_4$                          (Formula VI)

or Formula VIa $R^2X$                           (Formula VIa)

where X is halo and $R^2$ is defined above. The reaction is conducted under basic conditions, e.g., in the presence of an alkali metal carbonate or nitrogenous base. Where the etherifying agent is a halide ($R^2X$), the substrate of Formula V may be converted to the 3-hydroxy salt, and thereafter reacted with $R^2X$ in the presence of an amine compound serving as a hydrogen halide scavenger. Where a sulfate etherifying agent is used, the reaction is preferably conducted in an organic solvent medium, e.g., a low molecular weight ketone in the presence of an alkali metal carbonate at a moderately elevated temperature, conveniently the atmospheric reflux temperature of the organic solvent. Acetone is particularly suitable. A substantial molar excess of $(R^2)_2SO_4$ can be used to assure essentially quantitative conversion of the 3-hydroxy substrate of Formula V to the 3—$OR^2$ intermediate product of Formula IV. However, it may be desirable to avoid a substantial excess in order to minimize consumption of the sulfate diester which can be difficult to recover economically, and may need to be destroyed after the etherification reaction is complete, e.g., by addition of aqueous ammonia. Thereafter, the product may be recovered by filtering to remove alkali metal carbonate and any other solid alkali metal salts, adding water to the filtered reaction mass and extracting the compound of Formula IV with an organic solvent of limited miscibility with water, e.g., diethyl ether. Preferably, the extract is washed with an alkaline solution before removal of the solvent by evaporation. The residue may be partially refined by taking it up in another solvent, preferably a halogenated solvent, and drying and filtering the resulting solution. The halogenated solvent is then removed by evaporation. Drying may be accomplished before or during evaporation of solvent by contacting the solution with a dessicant such as $CaCl_2$ or by sparging with dry air or inert gas. The residue may be recrystallized as desired, preferably from a solvent comprising an alkane/ester mixture.

The compound of Formula IV is a novel compound having utility in the synthesis of monomers for polyamides, and potentially for synthesis of other useful products. For use in synthesis of monomers for polyamides that bind to DNA, preferences for the various substituents of the compound of Formula IV are the same as for compounds of Formula V.

The nitro group of the compound of Formula IV is then reduced to form a compound of Formula III

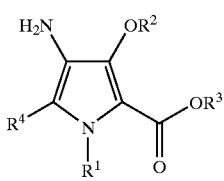

(Formula III)

wherein $R^1$, $R^2$ $R^3$ and $R^4$ are as defined above. Reduction of the nitro group may be accomplished by contacting the compound of Formula IV with a hydrogen transfer agent in the presence of a catalyst for the reduction reaction. A preferred catalyst is palladium, preferably on a carbon support. A typically suitable catalyst is 5% Pd/C or 10% Pd/C. A typical hydrogen transfer agents useful in the nitro reduction step is ammonium formate. The reaction is preferably conducted in an organic solvent, e.g., an ester such as ethyl acetate at moderately elevated temperature, conveniently at the atmospheric reflux temperature of the solvent. Alternatively, the reaction can be conducted in methanol at ambient temperature. A substantial excess of hydrogen transfer agent is preferably charged to the reaction to assure essentially quantitative reduction of the nitro group. An ester solvent such as ethyl acetate is especially preferred because it does not dissolve a hydrogen transfer agent such as ammonium formate, allowing excess transfer agent to be removed by filtration and recycled to the nitro reduction reactor. Reaction time is typically 20 to 60 minutes. The catalyst and excess undissolved hydrogen transfer agent are removed by filtration and the solvent evaporated, preferably under reduced pressure, for recovery of the product of Formula III.

Literature describing reduction of a nitro group on a heterocyclic ring with ammonium formate generally calls for a high weight ratio of catalyst to nitroheterocyclic substrate, e.g., a charge of 10% Pd/C catalyst essentially equal in weight to the substrate, or at least about 10% by weight Pd metal based on the substrate. In accordance with the invention, it has been discovered that reduction of the nitro group of compound IV can be accomplished using a relative low catalyst charge, i.e., a charge providing as low as 1% by weight Pd based on the substrate charge, or even lower. Preferably, the amount of catalyst charged to the reaction zone is between about 5% and about 1% by weight based on substrate, achieved for example by charging a 20% Pd/C catalyst in a proportion of between about 5% and about 25% by weight based on the substrate of Formula IV. The low catalyst charge provides advantages both in the consumption of catalyst and in facilitating the removal of catalyst by filtration.

Alternatively, reduction of the nitro group may be conducted by contacting the compound of Formula IV with hydrogen under pressure in the presence of a catalyst for the reaction. The same catalysts useful in the hydrogen transfer reaction can be used for catalytic hydrogenation. Substantially elevated hydrogen pressure is required for the reaction, e.g., 100 to 900 psig or higher. Conveniently, Formula IV substrate is charged to the reaction zone in an organic solvent solution. Reaction may be conducted at temperatures comparable to those used in the hydrogen transfer reaction.

The compounds of Formula III are novel compounds having utility in the synthesis of monomers for polyamides, and potentially for synthesis of other useful products. For use in synthesis of monomers for polyamides that bind to DNA, preferences for the various substituents of the compound of Formula III are the same as for compounds of Formula IV.

The compound of Formula III may be reacted with a blocking group reagent to produce a compound of Formula II

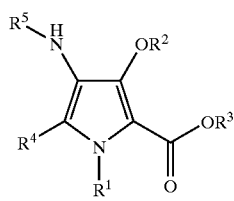

(Formula II)

wherein $R^5$ represents a carbamate-forming blocking group and $R^1$, $R^2$, $R^3$, and $R^4$ are as defined above. Preferably, the blocking group reagent is a dicarbonate ester corresponding to the Formula

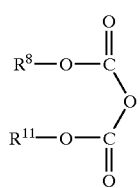

(Formula XIII)

where

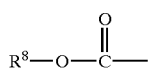

is $R^5$ and $R^{11}$ are independently selected from among substituted or unsubstituted alkyl (preferably $C_1$ to $C_6$), alkenyl (preferably $C_2$ to $C_6$), alkynyl (preferably $C_2$ to $C_6$), aralkyl or aryl, or substituted silyl. Preferred substituents which may constitute $R^8$ include t-butyl, fluorenylmethyl, allyl, trialkylsilylmethyl and benzyl. Other substituents which may constitute $R^8$ include those described above with respect to $R^2$ and $R^3$. Alternatively, the reaction may be conducted using an oxycarbonyl halide corresponding to the Formula $R^8OC(O)X$ where

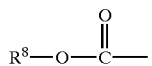

and $R^8$ are as defined above and X is halide.

In conducting the blocking reaction with a dicarbonate ester of Formula XIII, a solution of the compound of Formula III and dicarbonate ester is prepared, preferably in an aqueous solvent, more preferably in an acetone/water solvent mixture. Alternatively, another polar solvent, e.g., dioxane, can be used. Substantially quantitative blocking of the 4-amino group is promoted by charging at least a slight excess of the dicarbonate. The reaction proceeds satisfactorily at room temperature, preferably under neutral to basic conditions. The product may be recovered by extraction with a water-immiscible solvent, preferably a halogenated solvent such as dichloromethane, chloroform or 1,2- dichloroethane. The extract may be washed with water for removal of impurities, dried over a dessicant such as calcium chloride, or under vacuum or other convenient method, after which the solvent is removed by evaporation.

The compound of Formula II is converted to the compound of Formula I in a conventional manner, i.e., by saponification of the 2-carboxylate ester to the 2-carboxylic acid.

The overall synthesis of Reaction Scheme 1 thus proceeds according to the following series of reactions

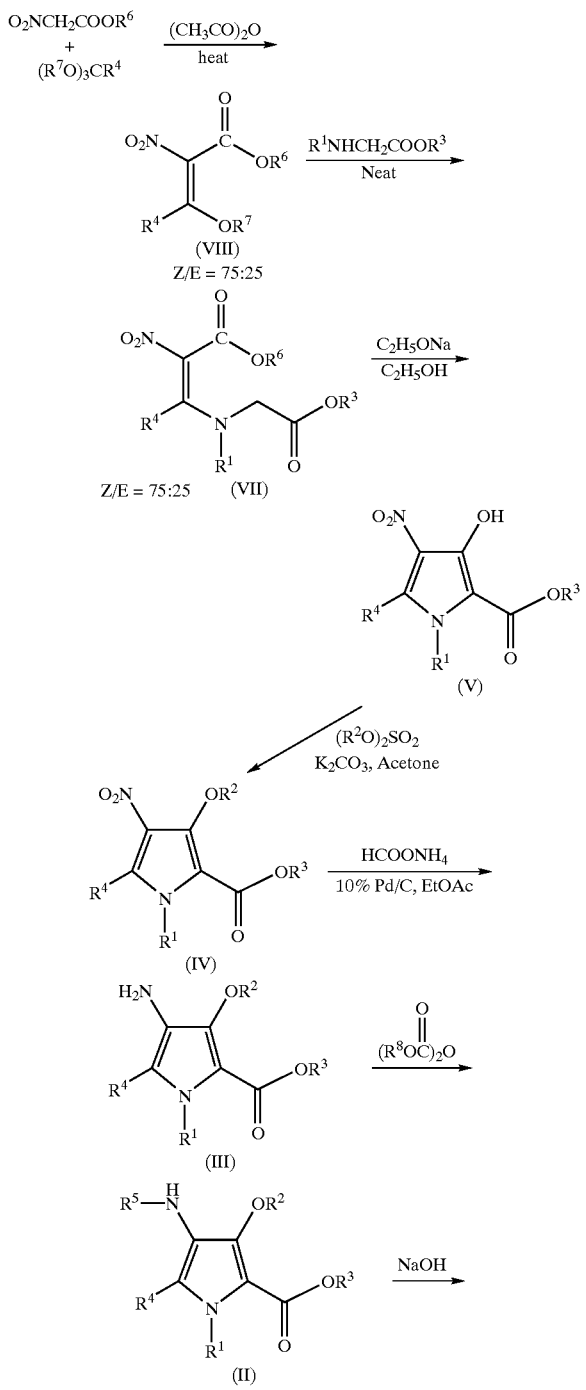

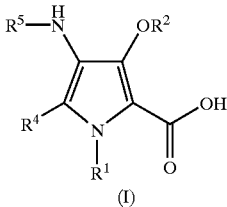

(I)

Reaction Scheme 2

Reaction scheme 2 proceeds in the same manner as reaction scheme 1 through the preparation of the intermediate compound of Formula V. The 4-nitro group of the compound of Formula V is then reduced to yield the compound of Formula XII

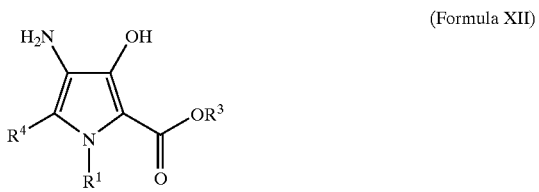

(Formula XII)

As in the conversion of the compound of Formula IV to the compound of Formula III per reaction scheme 1, reduction of the Formula V compound nitro group can be accomplished by reaction with a hydrogen transfer agent such as ammonium formate in the presence of a catalyst for the reaction such as 5% or 10% Pd/C. Alternatively, the nitro reduction can be effected by catalytic hydrogenation under elevated hydrogen pressure. In either case the conditions for the reaction are essentially identical to those applicable to the preparation of the compound of Formula III from the compound of Formula IV.

The compounds of Formula XII are novel compounds having utility in the synthesis of monomers for polyamides, and potentially for synthesis of other useful products. For use in synthesis of monomers for polyamides that bind to DNA, preferences for the various substituents of the compounds of Formula XII are the same as for compounds of Formula V.

A blocking group is then introduced as a substituent on the 4-amino group of the compound of Formula XII, yielding a compound of Formula XI

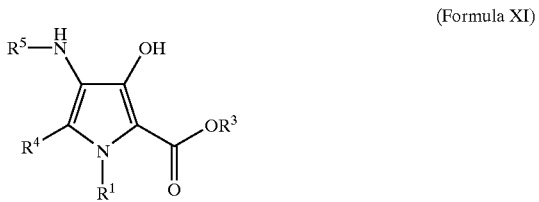

(Formula XI)

where $R^1$, $R^3$, $R^4$ and $R^5$ are as defined above. The reactions for preparation of the compound of Formula XI from the compound of Formula XII are the same as those described above per reaction scheme 1 for introducing a blocking group on the 4-amino substituent of the compound of Formula III to produce the compound of Formula II. Conditions for the reaction are also substantially the same as for the conversion of the Formula III compound to Formula II. In conversion of the compound of Formula XII to that of Formula XI, it is especially important to operate under neutral to acidic conditions to avoid reaction of the 3-hydroxyl group.

The compounds of Formula XI are novel compounds having utility in the synthesis of monomers for polyamides, and potentially for synthesis of other useful products. For use in synthesis of monomers for polyamides that bind to DNA, preferences for the substituents $R^1$, $R^3$, $R^4$ and $R^5$ of the compounds of Formula XI are the same as for compounds of Formula II.

The compound of Formula XI may be converted to the compound of Formula XIX by the same saponification reaction used for the conversion of the compound of Formula II to the compound of Formula I

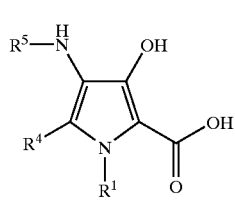

(Formula XIX)

Preferably, the 4-amino blocking substituent and N-substituent ($R^1$) of the compound of Formula XIX are the same as those of the compound of Formula I.

Although, the compound of Formula XIX may be used in the synthesis of polyamides, the 3-hydroxy group is preferably blocked also to prevent branching and crosslinking in the polymerization reaction. For this purpose, the compound of Formula XI is preferably reacted with a reagent which introduces such a protective group at the 3-position prior to saponification to the 2-carboxylic acid. The reagents and conditions for introduction of the protective group are the same as described above for the conversion of the compound of Formula V to the compound of Formula IV. When this reaction is conducted on the substrate of Formula XI, the O-protected product of the reaction is the compound of Formula II. Saponification of the compound of Formula II to the compound of Formula I is described above.

Thus, the overall synthesis of Reaction Scheme 2 is as follows

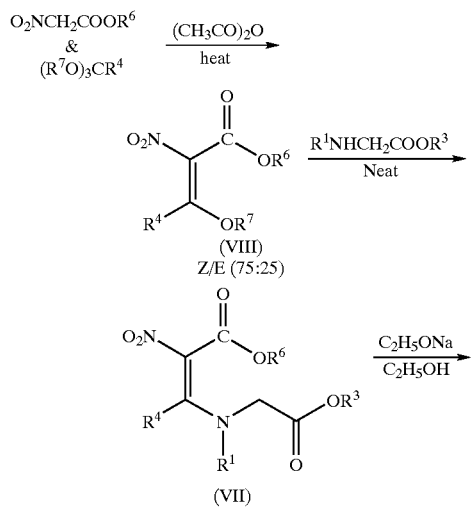

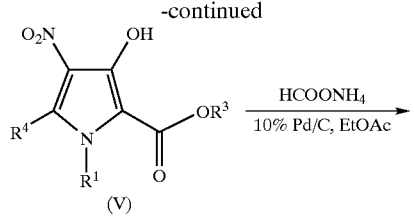

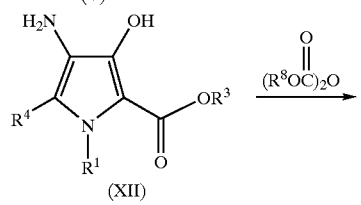

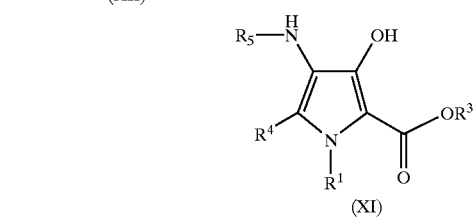

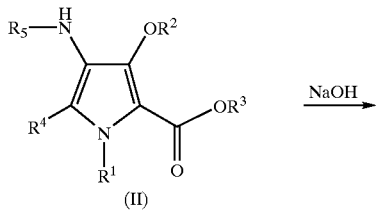

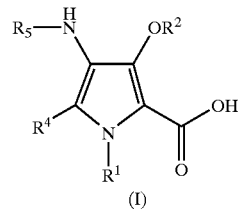

When polyamides produced from the monomers of Formula I or XXV are used in DNA recognition, the O-protective group $R^2$ must be removed. Although a methyl group functions effectively as the O-protective group $R^2$ in the polymerization reaction, removal of a methyl group requires harsh conditions. Substituents such as acyl, trialkylsilyl, benzyl and allyl may be preferred in some cases.

Novel compounds of Formulae III and XII may be generically defined by Formula XIV

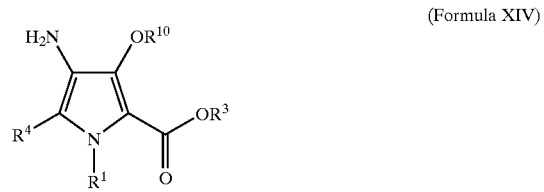

(Formula XIV)

and novel compounds of Formulae IV and V may be generically defined by Formula XV

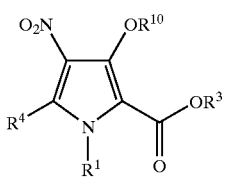

(Formula XV)

In each of Formulae XIV and XV $R^{10}$ includes all groups that may constitute $R^2$, plus hydrogen.

Reaction Scheme 3

In a further alternative reaction scheme of the invention, both the 3-hydroxy and 2-carboxy groups are blocked by formation of a fused ring compound of Formula XXII

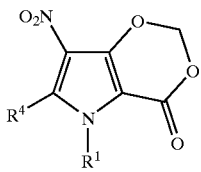

(Formula XXII)

where $R^1$ and $R^4$ are defined above. The intermediate of Formula XXII is formed by reacting the compound of Formula V with paraformaldehyde in the presence of a base, preferably a nitrogenous base such as N,N'-diisopropylethylamine (DIEA). The reaction may be carried out by heating the compound of Formula V with a several fold molar excess of paraformaldehyde in a polar solvent such as dimethylformamide or dimethyl sulfoxide at a temperature high enough to depolymerize the paraformaldehyde. Reaction temperature may typically range from about 25° C. to about 150° C.

The compound of Formula XXII is a novel intermediate useful in the synthesis of polyamides and potentially as an intermediate for other syntheses. Preferred substituents which may constitute $R^1$ are the same as those for the other intermediates as described hereinabove.

The 4-nitro group of the compound of Formula XXII is reduced by catalytic reaction with a hydrogen transfer agent or by catalytic hydrogenation in the manner and under the conditions described hereinabove for the conversion of the compound of Formula IV to the compound of Formula III, thereby yielding the 4-amino compound of Formula XXI

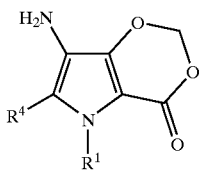

(Formula XXI)

wherein $R^1$ is as described above.

A blocking group is then introduced on the 4-amino group of the compound of Formula XXI to produce the compound of Formula XX

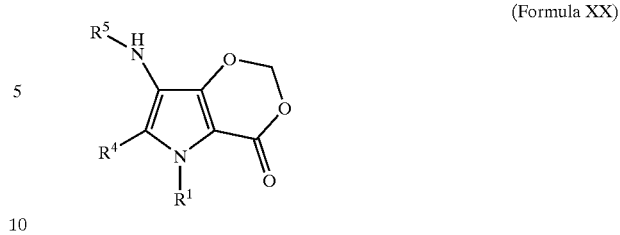

(Formula XX)

wherein $R^1$, $R^4$ and $R^5$ are as described above. Introduction of the blocking group is effected by the same reaction used to convert the compound of Formula III to the compound of Formula II. The reagents and conditions of the reaction are essentially the same as for the conversion of the compound of Formula III to Formula II, and the preferences in the nature of the blocking group are also the same.

The compounds of Formulae XX, XXI and XXII are novel compounds having utility in the synthesis of monomers for polyamides, and potentially for synthesis of other useful products. For use in synthesis of monomers for polyamides that bind to DNA, preferences for the substituents $R^1$ and $R^5$ of the compounds of Formulae XX, XXI and XXII are the same as for compounds of Formula II.

The compound of Formula XX may then be saponified to produce the compound of Formula XIX or a salt thereof. Saponification may be conducted by contacting the compound of Formula XX with 1–5 equivalents of an alkali metal hydroxide (e.g., LiOH, NaOH or KOH) in aqueous alcohol or aqueous DMSO. The reaction temperature may range from about 25° C. to about 100° C. and is preferably in the lower end of that range. LiOH is a preferred saponifying reagent.

The 3-hydroxy group may be protected by introducing an O-substituent with a trialkylsilyl chloride, aryl halide, or aryl anhydride and a suitable nitrogenous base in a nonpolar solvent. Suitable bases include pyridine, imidazole and trialkylamine. Suitable solvents include ethers, esters and haloalkanes.

Alternatively, the compound of Formula XIX may be reacted with a carboxylic acid anhydride of Formula XXVII

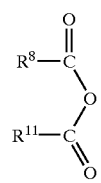

(Formula XXVII)

where $R^8$ and $R^{11}$ are as defined above and may be the same or different, to produce a compound of Formula XXIII

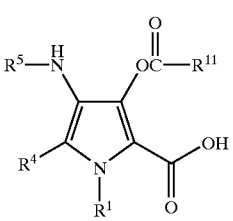

(Formula XXIII)

where $R^4$, $R^5$ and $R^{11}$ are as defined above. An acyl halide such as $R^{11}C(O)Cl$ or $R^{11}C(O)$ Br can also be used. According to a still further option, a compound of Formula XIX may be reacted with a dicarbonate diester of Formula XIII (Formula XIII)

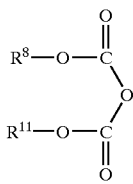

or the haloformate:

$R^8OC(O)X$ where $R^8$, $R^{11}$ and X are as defined above to produce a compound of Formula XXVI:

(Formula XXVI)

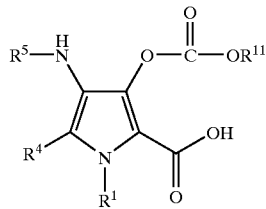

wherein $R^1$, $R^4$, and $R^5$ are as defined above. Preferably $R^5$ is $R^3$—O—C(O)—, where $R^8$ is as defined above.

In accordance with a further alternative, the compound of Formula XIX may be reacted with a trialkylsilyl halide in the presence of a nitrogenous base to yield a compound of Formula XXIV:

(Formula XXIV)

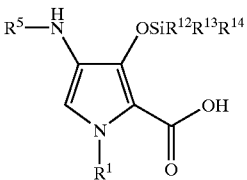

wherein $R^{12}$, $R^{13}$, and $R^{14}$ are independently $C_1$ to $C_6$ alkyl and $R^1$, $R^4$ and $R^5$ are as defined above. Again, $R^5$ is preferably $R^8$—O—C(O)—.

The compounds of Formulae XXIII and XXIV are also novel compounds useful in the synthesis of monomers for polyamides, and potentially for synthesis of other useful products. For use in synthesis of monomers for polyamides that bind to DNA, preferences for the substituents $R^1$ and $R^5$ of the compound of Formulae XX, XXI and XXII are the same as for compounds of Formula II.

Thus, the overall synthesis of Reaction Scheme 3 is as follows:

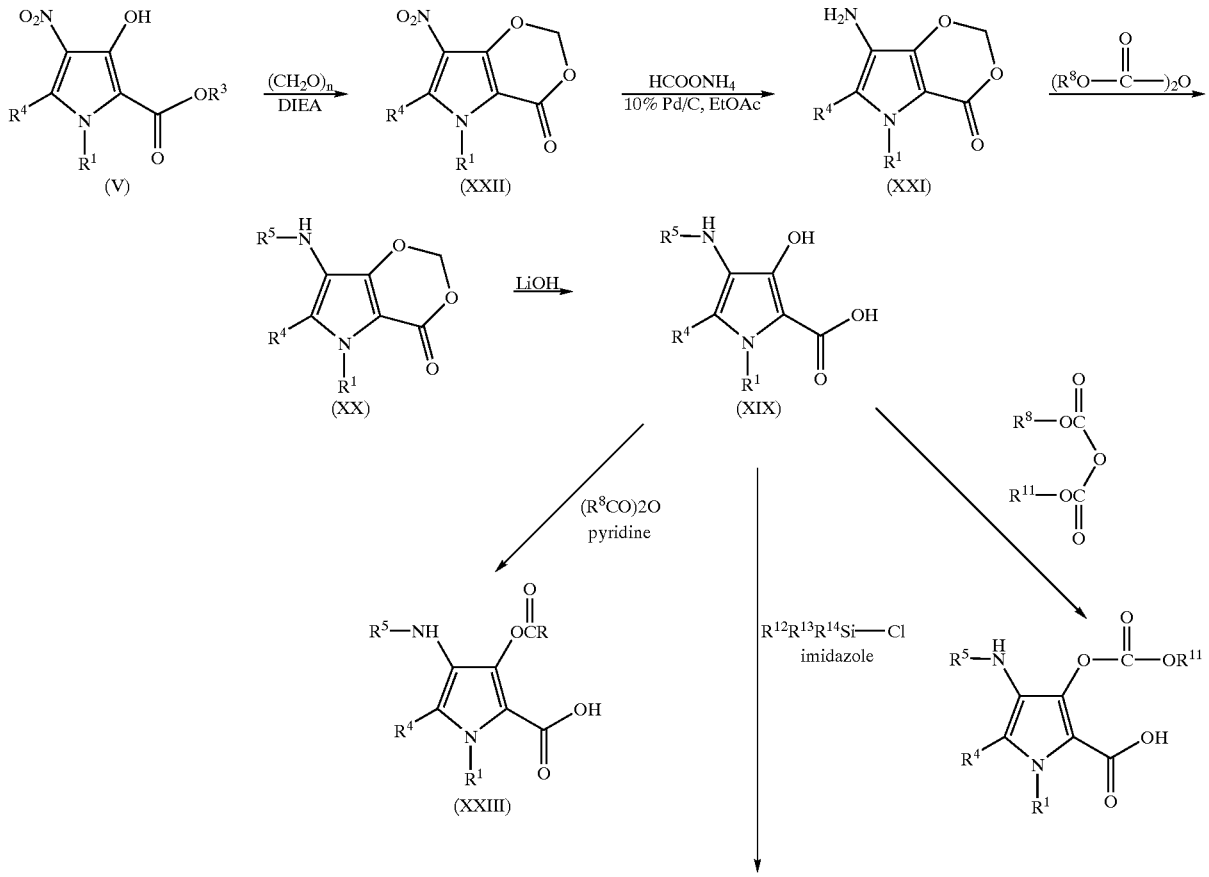

-continued

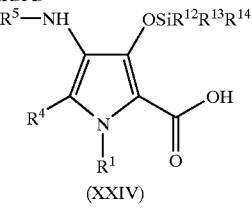
(XXIV)

In providing the 4-amino group by reduction of a 4-nitro group, each of the above-described reaction schemes avoids the problem of 4-decarboxylation which is encountered when water is present in the synthesis of a blocked 4-amino group according the reaction scheme disclosed by Momose et al., supra.

Further in accordance with the present invention, another alternative reaction scheme is provided which can utilize a starting material comprising a 4-carboxyl pyrrole derivative.

Reaction Scheme 4

In reaction scheme 4 a compound corresponding to the Formula III:

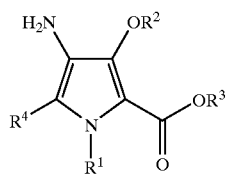
(Formula III)

wherein:

$R^1$, $R^2$, $R^3$ and $R^4$ are as defined above;
is reacted with a carbonyl compound under conditions effective for the reaction of the 4-amino group of the compound of Formula III with the carbonyl compound, to produce a 4-isocyanate compound of Formula XVII:

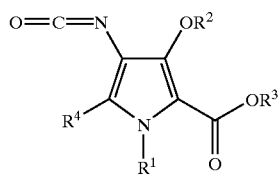
(Formula XVII)

wherein $R^1$, $R^2$, $R^3$, and $R^4$ are as defined above. The carbonyl compound that reacts with the compound of Formula III is preferably a carbonyl compound comprising two leaving groups, more preferably a carbonyl dihalide such as phosgene, a phosgene dimer, i.e., trichloromethyl chloroformate, or a phosgene trimer, i.e., bis(trichloromethyl)carbonate. According to a still further alternative, the isocyanate may be formed by reacting the 4-amino group with $CO_2$ in the presence of a dehydrating agent such as $P_2O_5$. The 4-isocyanate compound of Formula XVII may then reacted with an alcohol, e.g., t-butyl or benzyl alcohol to yield the compound of Formula XVI

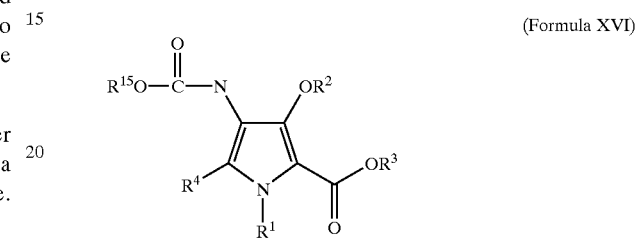
(Formula XVI)

wherein $R^{15}$ is unsubstituted alkyl (preferably $C_1$ to $C_6$), alkenyl (preferably $C_2$ to $C_6$), alkynyl (preferably $C_2$ to $C_6$), aralkyl or aryl, or substituted silyl; and $R^1$, $R^2$, $R^3$ and $R^4$ are as defined above. In carrying out this reaction, the isocyanate of Formula XVII is heated with a 1–5 fold molar excess of the alcohol in an aromatic solvent (e.g., toluene or xylene) in the presence of a nitrogenous base catalyst such as trialkylamine.

The compounds of Formula XVII are novel compounds having utility in the synthesis of monomers for polyamides, and potentially for synthesis of other useful products. For use in synthesis of monomers for polyamides that bind to DNA, preferences for the substituents $R^1$, $R^2$, $R^3$, and $R^4$ are the same as for compounds of Formula II, and the preferences are the same as the preferences for $R^2$ in Formula II.

The overall synthesis of Reaction Scheme 4 is as follows:

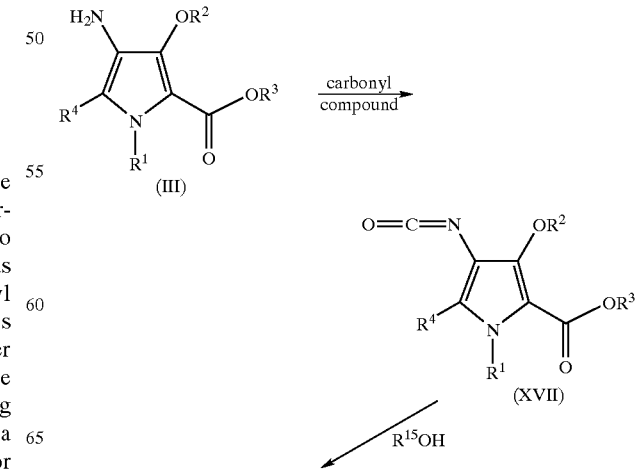

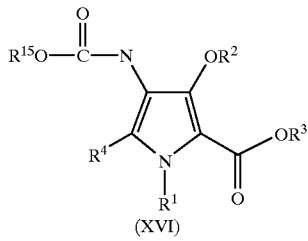

(XVI)

In a more preferred reaction scheme, the isocyanate of Formula XVII may be used directly in the preparation of polyamides. The isocyanate moiety of one monomer molecule reacts with the 2-carboxylate of another to form the amide linkage with extrusion of $CO_2$.

The following examples illustrate the reactions.

Experimental

Instrumentation and General Methods.

$^1$H and $^{13}$C were recorded on a Varian VXR-300 ($^1$H, 300 MHZ and $^{13}$C, 75.4 MHZ) or a Varian INOVA ($^1$H, 400 MHZ and $^{13}$C, 100 MHZ) spectrometer in $CDCl_3$ or DMSO-$d_6$ as solvent unless otherwise stated. All NMR data are reported in ppm or d values downfield from tetramethylsilane (TMS, d=0.00, as an internal reference) and coupling constants, J, are reported in Hz. $^{13}$C NMR spectra were proton decoupled and recorded in $CDCl_3$. The center peak of the solvent $CDCl_3$ at 77.00 ppm was used as an internal reference. The multiplicities of the $^{13}$C NMR signals were determined by the attached proton test (APT) pulse sequence. Electron impact (EI) and chemical ionization (CI) mass spectra were recorded, at 70 eV ionizing voltage, on a Hewlett-Packard 5988A twin EI and CI quadrupole mass spectrometer connected to a Hewlett-Packard 5890A gas chromatograph fitted with a Hewlett-Packard 12 m×0.33 mm Ultra-1 (cross-linked methyl silicone) column.

Low resolution liquid chromatography-mass spectrometry (LC-MS) experiments were performed utilizing a Hewlett Packard 1100 HPLC system and a Micromass Platform LCZ single quadrupole mass spectrometer with Electrospray as the ion source was operated in positive or negative mode. Exact mass measurements were performed on a Mariner T Biospectrometry™ Workstation (Perceptive Biosystems, Inc.), time of flight (TOF) mass spectrometer. Molecular weight measurements have mass accuracies +/−100 ppm of the theoretical mass utilizing an external calibrant. The mass spectrometer was operated in positive mode using electrospray as the ion source.

Solutions were evaporated under reduced pressure with a rotary evaporator, and the residues were flash chromatographed on a silica gel column using an ethyl acetate/hexane mixture as the eluent unless specified otherwise. Chromatographic separations on the Chromatotron were accomplished using 2 mm or 4 mm Kieselgel 60 $PF_{254}$ gypsum coated plates. Analytical thin-layer chromatography (TLC) analyses were performed on EM silica gel plates, $60PF_{254}$. Visualization was accomplished with UV light or iodine. Melting points were determined on a Dynamics Optics AHT 713921 hot-stage apparatus and are uncorrected. Microanalyses were performed by Atlantic Microlab, Inc., Norcross, Ga.

Materials and Reagents.

Sarcosine ethyl ester hydrochloride, triethylamine, ethyl nitroacetate, triethyl orthoformate, acetic anhydride, ethyl acetate, hexane, toluene, dimethyl sulfate, ammonium formate, Pd on activated charcoal (10%) and di-tert-butyldicarbonate, were obtained from Aldrich and used as such. Methylene chloride, dioxane, acetone, and tert-butyl alcohol were obtained from EM Science. Absolute ethyl alcohol (AAPER), sodium metal (Fisher), sodium hydroxide (J. T. Baker), ammonia (Matheson), diethyl ether and potassium carbonate (Mallinckrodt) were reagent grade and used as received.

Ethyl Sarcosinate ($CH_3NHCH_2COOC_2H_5$)

The liberation of the free ester from its hydrochloride salt was accomplished by passing dry ammonia gas through a suspension of sarcosine ethyl ester hydrochloride (50 g, 325.5 mmol) in diethyl ether (600 mL) at 0° C. (ice-bath) for 3 h. Precipitated ammonium chloride was removed by filtration and washed with ether. The filtrate was concentrated, first by rotary evaporation and then on a vacuum pump for 30 min afforded ethyl sarcosinate as a pale pink liquid (38.55 g, 100%); $^1$H NMR (300 MHZ, $CDCl_3$) d 1.28 (t, J=7.1 Hz, 3H, $CH_3$—$CH_2$—), 1.60 (s, 1H, $CH_3$—NH—), 2.44 (s, 3H, $CH_3$—NH—), 3.36 (s, 2H, —NH—$CH_2$—), 4.20 (q, J=7.1 Hz, 2H, $CH_3$—$CH_2$—); $^{13}$C NMR (75.4 MHZ, $CDCl_3$) d 14.19, 36.08, 52.65, 60.62, 172.32.

EXAMPLE 1

Ethyl Ethoxymethylenenitroacetate

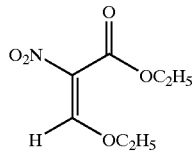

A mixture of ethyl nitroacetate (30 g, 225.4 mmol), triethyl orthoformate (75 mL, 450 mmol) and acetic anhydride (61 mL, 640 mmol) were heated for 1 h at 120° C. and for a further 1 h at 130° C. in a distillation apparatus. The reaction mixture was finally heated at 140° C. and the distillate (~100 mL) was collected. The excess of triethyl orthoformate and acetic anhydride was removed under reduced pressure to give a dark orange viscous liquid (41.4 g). Fractional distillation of the crude product under reduced pressure (105–106° C./0.2 mm Hg) afforded a light yellow liquid (33.87 g, 79%). GC and $^1$H NMR analysis of the purified product indicated the presence of Z,E-isomers in a 73:27 ratio.

(Z)-isomer: $^1$H NMR (400 MHZ, $CDCl_3$) d 1.31 (t, J=7.2 Hz, 3H, $CH_3$—$CH_2$—), 1.43 (t, J=7.2 Hz, 3H, $CH_3$—$CH_2$), 4.30 (q, J=7.2 Hz, 2H, $CH_3$—$CH_2$—), 4.31 (q, J=7.2 Hz, 2H, $CH_3$—$CH_2$—), 7.52 (s, 1H); $^{13}$C NMR (100 MHZ, $CDCl_3$) d 14.05, 15.11, 61.88, 73.93, 127.01, 155.94, 159.81; MS (EI, 70 eV) m/z (relative intensity) 190 (M+1, 5), 189 (M$^+$, 49), 172 (36), 161(6), 144 (60), 117 (19), 116 (55), 115 (100), 99 (61), 88 (63), 87 (54), 86 (70), 71 (85), 70 (56), 54 (33), 43 (28), Calcd for $C_7H_{11}NO_5$: 189.18. (E)-isomer: $^1$H NMR (400 MHZ, $CDCl_3$) d 1.34 (t, J=7.2 Hz, 3H, $CH_3$—$CH_2$—), 1.46 (t, J=7.2 Hz, 3H, $CH_3$—$CH_2$), 4.35 (q, J=7.2 Hz, 2H, $CH_3$—$CH_2$—), 4.36 (q, J=7.2 Hz, 2H, $CH_3$—$CH_2$—), 8.22 (s, 1H); $^{13}$C NMR (100 MHZ, $CDCl_3$) d 13.92, 15.15, 61.97, 74.60, 129.35, 159.06, 162.86; MS (EI, 70 eV) m/z (relative intensity) 190 (M+1, 5), 189 (M$^+$, 37), 172 (30), 161(7), 144 (96), 117 (19), 116 (65), 115 (100), 99 (56), 88 (62), 87 (51), 86 (77), 71 (93), 54 (35), 43 (23), Calcd for $C_7H_{11}NO$: 189.18.

EXAMPLE 2

Ethyl-N-[(2-(nitro-2-ethoxycarbonyl)vinyl] sarcosinate

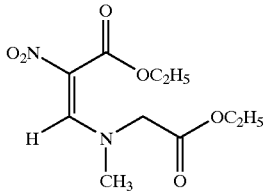

Ethyl sarcosinate (3.30 g, 28.17 mmol) was added to ethyl ethoxymethylenenitroacetate (5.26 g, 27.80 mmol) at room temperature, an exothermic reaction occurred and a dark orange red solution was obtained. The reaction mixture was stirred at room temperature for 2 h. Ethanol was removed by rotary evaporation to afford an orange red oily liquid (7.186 g, 99%): MS (EI, 70 eV) m/z (relative intensity) 261 (M+1, 1), 260 (M$^+$, 12), 214 (10), 187 (37), 159 (100), 142 (24), 113 (41), 85 (72), 69 (17), 42(70), Calcd for $C_{10}H_{16}N_2O_6$: 260.25.

EXAMPLE 3

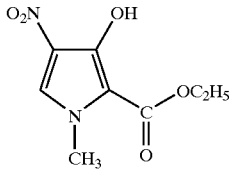

Ethyl 1-methyl-4-nitro-3-hydroxypyrrole-2-carboxylate

To a solution of ethyl-N-[(2-nitro-2-ethoxycarbonyl) vinyl]sarcosinate (32.12 g, 123.42 mmol) in abs. ethanol (150 mL) was added a solution of sodium ethoxide prepared from sodium (4.0 g, 174.0 mmol) and abs. ethanol (100 mL). The reaction mixture was refluxed under a nitrogen atmosphere for 2 h to afford a dark orange-brown solution. Ethanol was removed under reduced pressure to give a dark brown residue. The residue was dissolved in water (500 mL) and acidified with 20% $H_2SO_4$ to give a brown precipitate, filtered and washed with water. The filtrate was extracted with $CH_2Cl_2$ (10×100 mL). The brown solid was dissolved in $CH_2Cl_2$ and the solution was mixed with $CH_2Cl_2$ extracts. The combined extracts were dried with anhydrous $Na_2SO_4$. Filtration and rotary evaporation gave an orange brown solid (11.28 g). The residue was dissolved in $CH_2Cl_2$ (250 mL) and passed through a pad of Silica gel (100 g), washed several times with $CH_2Cl_2$, evaporation of the solvent gave an orange crystalline solid (5.60 g, 21.2%). Recrystallization from ethyl acetate/hexane afforded very pale yellow needles; mp 126–128° C.; $^1$H NMR (300 MHZ, CDCl$_3$) d 1.41 (t, J=7.2 Hz, 3H, CH$_3$—CH$_2$—), 3.88 (s, 3H, CH$_3$—N—), 4.41 (q, J=7.2 Hz, 2H, CH$_3$—CH$_2$—), 7.40 (s, 1H, H-5), 8,85 (s, 1H, —OH); $^{13}$C NMR (100 MHZ, CDCl$_3$) d 14.35, 38.77, 61.06, 107.45, 123.44, 125.24, 147.42, 161.52; MS (EI, 70 eV) m/z (relative intensity) 215 (M+1, 3), 214 (M$^+$, 30), 169 (19),

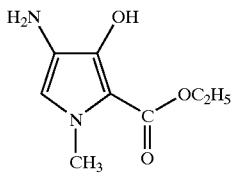

168 (100), 152 (26), 140 (14), 94 (8), 53 (19), 42 (11), Calcd for $C_8H_{10}N_2O_5$: 214.18. HRMS: Calcd for $C_8H_{11}N_2O_5$ [M+H$^+$]215.0668, Found; 215.0666. Anal. Calcd for $C_8H_{10}N_2O_5$: C, 44.86; H, 4.70; N, 13.07. Found: C, 44.97; H, 4.76; N, 12.97. TLC (ethyl acetate) R$_f$ 0.44.

EXAMPLE 4

Ethyl 1-methyl-4-amino-3-hydroxypyrrole-2-carboxylate

To a solution of ethyl 1-methyl-4-nitro-3-hydroxypyrrole-2-carboxylate (0.90 g, 4.20 mmol) in ethyl acetate (50 mL) was added ammonium formate (2.64 g, 41.86 mmol) and 10% Pd/C (1.20 g) and the reaction mixture was refluxed under a nitrogen atmosphere for 30 min. The reaction mixture was filtered through a bed of Celite, washed with ethyl acetate (2×50 mL). The solvent was evaporated under reduced pressure to afford the crude product as a dirty yellow solid (0.664 g, 86%); $^1$H NMR (300 MHZ, CDCl$_3$) d 1.37 (t, J=7.2 Hz, 3H, CH$_3$—CH$_2$—), 3.66 (s, 3H, CH$_3$—N—), 4.35 (q, J=7.2 Hz, 2H, CH$_3$—CH$_2$—), 6.26 (s, 1H, H-5); $^{13}$C NMR (100 MHZ, CDCl$_3$) d 14.37, 36.38, 59.67, 105.23, 116.49, 118.72, 145.22, 162.46; MS (EI, 70 eV) m/z (relative intensity) 185 (M+1, 3), 184 (M$^+$, 35), 139 (16), 138 (100), 137 (16), 110 (25), 109 (9), 82 (9), 55 (9), 42 (10), Calcd for $C_8H_{12}N_2O_3$: 184.19. TLC (ethyl acetate) R$_f$ 0.27. Above sample was used for the preparation of ethyl 1-methyl-4-(tert-butoxycarbonyl) amino-3-hydroxypyrrole-2-carboxylate.

EXAMPLE 5

Ethyl 1-methyl-4-nitro-3-methoxypyrrole-2-carboxylate

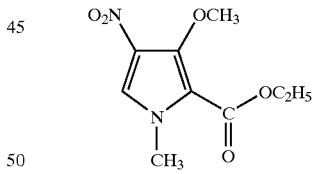

A mixture of ethyl 1-methyl-4-nitro-3-hydroxypyrrole-2-carboxylate (0.071 g, 0.3315 mmol), dimethyl sulfate (0.055 g, 0.436 mmol) and anhydrous potassium carbonate (0.5 g, 3.90 mmol) in dry acetone (20 mL) was refluxed under a nitrogen atmosphere for 22 h. Potassium carbonate was removed by filtration and the filtrate was evaporated under reduced pressure to afford an orange crystalline solid. Excess dimethyl sulfate was destroyed by treating the residue with aqueous ammonia (1 mL). Water (2 mL) was added and the residue was extracted with ether (30 mL). The combined ether extracts were washed with aqueous sodium hydroxide solution and water. Removal of ether under reduced pressure afforded a cream residue. The residue was dissolved in $CH_2Cl_2$ (25 mL), dried with anhydrous $Na_2SO_{4}$, filtered and evaporated under reduced pressure to yield a cream microcrystalline solid (0.067 g, 89%). Recrystallization from acetone/hexane afforded colorless needles, mp 145–147° C.; $^1$H NMR (300 MHZ, CDCl$_3$) d 1.40 (t, J=7.2 Hz, 3H, CH$_3$—CH$_2$—), 3.90 (s, 3H, CH$_3$—N—), 3.95 (s, 3H, CH$_3$O—), 4.36 (q, J=7.0 Hz, 2H, CH$_3$—CH$_2$—), 7.47 (s, 1H, H-5); $^{13}$C NMR (100 MHZ, CDCl$_3$) d 14.22, 38.92, 60.67, 63.02, 114.73, 125.76, 127.79, 146.18, 160.09; MS (EI, 70 eV) m/z (relative intensity) 229 (M+1, 3), 228 (M$^+$, 30), 211 (12), 183 (12), 167 (20), 153 (25), 152 (100), 141 (7), 109 (12), 84 (8), 67 (6), 53 (31), 42 (17), Calcd for C$_9$H$_{12}$N$_2$O$_5$: 228.20. HRMS (M+H): Calcd for C$_9$H$_{13}$N$_2$O$_5$ [M+H$^+$]: 229.0824, Found 229.0834. Anal. Calcd for C$_9$H$_{12}$N$_2$O$_5$: C, 47.37; H, 5.29; N, 12.27. Found. C, 47.44; H, 5.36; N, 12.28. TLC (ethyl acetate/Hexane, 1:3) R$_f$ 0.23.

EXAMPLE 6

Ethyl 1-methyl-4-amino-3-methoxypyrrole-2-carboxylate

To a solution of ethyl 1-methyl-4-nitro-3-methoxypyrrole-2-carboxylate (3.34 g, 14.64 mmol) in ethyl acetate (150 mL) was added ammonium formate (9.23 g, 146.37

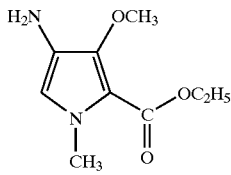

mmol) and 10% Pd/C (4.5 g) and the reaction mixture was refluxed under a nitrogen atmosphere for 30 min. The reaction mixture was filtered through a bed of Celite, washed with ethyl acetate (50 mL). The solvent was evaporated under reduced pressure to afford the product as an orange viscous liquid (2.753 g, 95%); $^1$H NMR (300 MHZ, CDCl$_3$) d 1.37 (t, J=7.1 Hz, 3H, CH$_3$—CH$_2$—), 2.87 (br s, 2H, —NH$_2$), 3.74 (s, 3H, CH$_3$—N—), 3.82 (s, 3H, —OCH$_3$), 4.31 (q, J=7.2 Hz, 2H, CH$_3$—CH$_2$—), 6.26 (s, 1H, H-5); MS (EI, 70 eV) m/z (relative intensity) 199 (M+1, 5), 198 (M$^+$, 41), 183 (8), 137 (100), 109 (6), 81 (5), 54 (6), 42 (8), Calcd for C$_9$H$_{14}$N$_2$O$_3$: 198.22. TLC (ethyl acetate) R$_f$ 0.20.

EXAMPLE 7

Ethyl 1-methyl-4-(tert-butoxycarbonyl) amino-3-methoxypyrrole-2-carboxylate

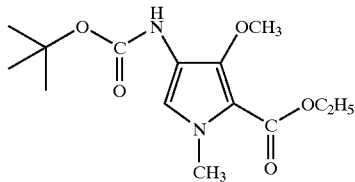

A solution of ethyl 1-methyl-4-amino-3-methoxypyrrole-2-carboxylate (2.75 g, 13.873 mmol) and di-tert-butyldicarbonate (3.37 g, 15.441 mmol) in dioxane (15 mL) was stirred at room temperature under a nitrogen atmosphere for 22 h. The solvent was removed under reduced pressure and the residue was treated with water (100 mL) and the mixture was extracted with CH$_2$Cl$_2$ (100 mL). The CH$_2$Cl$_2$ layer was washed with water and dried with anhydrous Na$_2$SO$_4$ filtered and the solvent was removed on a rotary evaporator to give an orange viscous liquid (4.888 g). $^1$H NMR of the crude residue indicated the presence of a sufficiently pure sample of ethyl 1-methyl-4-(tert-butoxycarbonyl)amino-3-methoxypyrrole-2-carboxylate contaminated with a trace of di-tert-butyldicarbonate. $^1$H NMR of the crude residue was identical with that of an authentic sample.

EXAMPLE 8

4-[(tert-Butoxycarbonyl)amino]-1-methyl-3-methoxypyrrole-2-carboxylic Acid

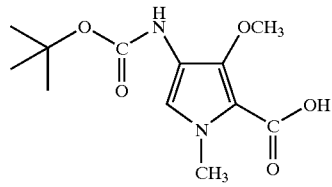

Crude ethyl 1-methyl-4-(tert-butoxycarbonyl)amino-3-methoxypyrrole-2-carboxylate (4.88 g, 16.38 mmol) was dissolved in ethanol (16 mL) and a solution of sodium hydroxide, prepared from NaOH (1.376 g) in water (15 mL), was added and the reaction mixture was stirred at room temperature for six days. Ethanol was removed under reduced pressure. Water (50 mL) was added and the solution was extracted with ether (2×50 mL) to remove any unreacted starting ester (0.183 g). The aqueous layer was acidified with H$_2$SO$_4$ to pH 2–3 to afford a colorless precipitate. The precipitated product was extracted with ether, dried with anhydrous Na$_2$SO$_4$. Filtration and rotary evaporation gave a dirty cream crystalline solid (2.922 g); $^1$H NMR (400 MHZ, DMSO-d$_6$) d 1.42 (s, 9H, (CH$_3$)$_3$C—), 3.67 (s, 3H, CH$_3$N—), 3.69 (s, 3H, CH$_3$O—), 6.96 (br s, 1H), 8.32 (br s, 1H), 12.10 (br s, 1 H, —COOH). 4-[(tert-Butoxycarbonyl) amino]-1-methyl-3-methoxypyrrole-2-carboxylic acid prepared by the above new method was identical in all aspects with the authentic sample.

EXAMPLE 9

Ethyl 1-methyl-4-(tert-butoxycarbonyl) amino-3-hydroxypyrrole-2-carboxylate (From Ethyl 1-methyl-4-amino-3-hydroxypyrrole-2-carboxylate)

The BOC group introduction was carried out in the presence of N,N-diisopropylethylamine by an error which resulted in the formation of an O,N-bis-BOC protected derivative: ethyl 1-methyl-4-(tert-butoxycarbonyl)amino-3-(tert-butoxycarbonyl)oxypyrrole-2-carboxylate.

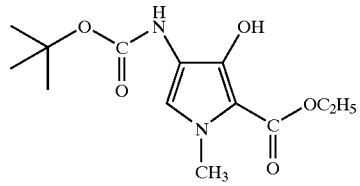

A solution of ethyl 1-methyl-4-amino-3-hydroxypyrrole-2-carboxylate (0.650 g, 3.529 mmol), N,N-diisopropylethylamine(1 mL, 5.741 mmol) and di-tert-butyldicarbonate (1.0 g, 4.615 mmol) in dioxane (7 mL) was stirred at room temperature under a nitrogen atmosphere for 19 h. The solvent was removed under reduced pressure and the residue was treated with water (50 mL) and the mixture was extracted with diethyl ether (3×50 mL). The ether layer was washed with water and dried with anhydrous $Na_2SO_4$, filtered and the solvent was removed on a rotary evaporator to give an orange brown paste (1.115 g). $^1$H NMR of the crude residue indicated the presence of two products: ethyl 1-methyl-4-(tert-butoxycarbonyl)amino-3-hydroxypyrrole-2-carboxylate and ethyl 1-methyl-4-(tert-butoxycarbonyl) amino-3-(tert-butoxycarbonyl)oxypyrrole-2-carboxylate (an O,N-bis-BOC protected derivative). Purification of the residue by radial chromatography on the Chromatotron using silica gel plate and elution with ethyl acetate/hexane (10/90) afforded ethyl 1-methyl-4-(tert-butoxycarbonyl)amino-3-hydroxypyrrole-2-carboxylate as a colorless crystalline solid (0.377 g, 38%) which was identical in all aspects ($^1$H, $^{13}$C NMR and MS) with the authentic sample of ethyl 1-methyl-4-(tert-butoxycarbonyl) amino-3-hydroxypyrrole-2-carboxylate prepared by the curtius reaction.

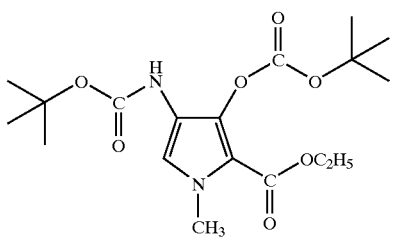

Further elution with the same solvent system afforded ethyl 1-methyl-4-(tert-butoxy carbonyl)amino-3-(tert-butoxycarbonyl)oxypyrrole-2-carboxylate as a colorless waxy solid (0.503 g, 37%). $^1$H NMR (300 MHZ, CDCl$_3$) d 1.33 (t, J=7.0 Hz, 3H, CH$_3$—CH$_2$—), 1.50 (s, 9H, (CH$_3$)$_3$C—), 1.56 (s, 9H, (CH$_3$)$_3$C—), 3.83 (s, 3H, CH$_3$—N—), 4.28 (q, J=7.0 Hz, 2H, CH$_3$—CH$_2$—), 6.14 (br s, 1H), 7.12 (br s, 1H, H-5), $^{13}$C NMR (100 MHZ, CDCl$_3$) d 14.42, 27.66, 28.27, 37.54, 59.96, 80.50, 83.87, 111.11, 114.78, 117.66, 141.48, 151.17, 152.73, 160.06; MS (EI, 70 eV) m/z (relative intensity) 285 (M+1-BOC, 0.3), 284 (M+−BOC, 4), 228 (12), 182 (18), 138 (100), 110 (4), 57 (58); Calcd for $C_{18}H_{28}N_2O_7$: 384.43. LRMS: Found; 407 [M+Na$^+$]. Calcd for $C_{18}H_{28}N_2O_7Na$: 407.

What is claimed is:

1. A process for the preparation of a compound of Formula II:

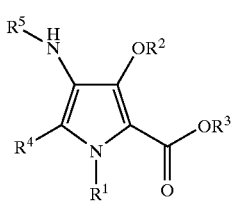

(Formula II)

wherein:
$R^1$ and $R^3$ are independently selected from the group consisting of substituted and unsubstituted alkyl, alkenyl, alkynyl, aralkyl and aryl;
$R^2$ is selected from the group consisting of substituted and unsubstituted alkyl, alkenyl, alkynyl, aralkyl, aryl, haloalkylcarbonyl, alkylcarbonyl, aralkylcarbonyl, arylcarbonyl, alkoxycarbonyl, alkenoxycarbonyl, alkynoxycarbonyl, aralkoxycarbonyl, and aryloxycarbonyl, and substituted silyl;
$R^4$ is selected from the group consisting of hydrogen and methyl; and
$R^5$ represents a carbamate-forming blocking group the process comprising:
reducing the nitro group of a compound of Formula IV

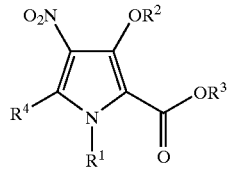

(Formula IV)

wherein $R^1$, $R^2$, $R^3$ and $R^4$ are as defined above, thereby producing a compound of Formula III

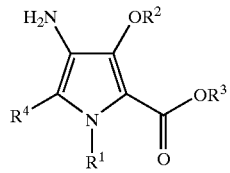

(Formula III)

wherein $R^1$, $R^2$, $R^3$ and $R^4$ are as defined above; and contacting said compound of Formula III with a blocking group reagent thereby substituting a blocking group on the 4-amino group.

2. A process as set forth in claim 1 wherein said blocking group is selected from the group consisting of t-butoxycarbonyl, fluorenylmethoxycarbonyl, allyloxycarbonyl, trialkylsilylethoxycarbonyl, and benzyloxycarbonyl.

3. A process as set forth in claim 2 wherein said blocking group is introduced by contacting said compound of Formula III with a blocking reagent selected from the group consisting of di(t-butyl)dicarbonate, t-butoxycarbonyl halide, di(fluorosceinylmethyl)dicarbonate, fluorenylmethoxycarbonyl halide, di(allyl) dicarbonate, allyloxycarbonyl halide, di(benzyl) dicarbonate and benzyloxycarbonyl halide.

4. A process as set forth in claim 1 wherein said nitro reduction comprises contacting said compound of Formula IV with a hydrogen transfer agent in the presence of a catalyst for the reduction reaction.

5. A process as set forth in claim 4 wherein said nitro reduction comprises introducing said compound of Formula IV and a palladium catalyst into a reaction zone, the proportion of palladium introduced into said reaction zone relative to said compound of Formula IV being not greater than about 2% by weight.

6. A process as set forth in claim 1 wherein said nitro reduction comprises contacting said compound of Formula IV with hydrogen under pressure in the presence of a catalyst for the reaction.

7. A process as set forth in claim 1 comprising contacting said compound of Formula III with a compound of Formula XIII under acidic or neutral conditions, said compound of Formula XIII having the structure:

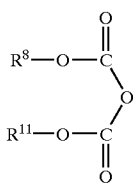

(Formula XIII)

wherein $R^8$ and $R^{11}$ are independently selected from the group consisting of substituted and unsubstituted alkyl, alkenyl, alkynyl, aralkyl and aryl, silylalkyl and substituted silyl.

8. A process as set forth in claim 1 wherein said blocking reagent corresponds to the formula:

$R^8$—OC(O)X wherein X is halo $R^8$ is selected from the group consisting of substituted and unsubstituted alkyl, alkenyl, alkynyl, aralkyl and aryl, silylalkyl and substituted silyl; and X is halide.

\* \* \* \* \*